United States Patent [19]

Baumann et al.

[11] Patent Number: 6,162,427

[45] Date of Patent: *Dec. 19, 2000

[54] COMBINATION OF G-CSF WITH A CHEMOTHERAPEUTIC AGENT FOR STEM CELL MOBILIZATION

[75] Inventors: Matthias Baumann, Karl-Ludwig-Strasse; Peter-Paul Ochlich, Wallonenstrasse, both of Germany

[73] Assignee: Roche Diagnostics GmbH, Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/091,401

[22] PCT Filed: Dec. 12, 1996

[86] PCT No.: PCT/EP96/05568

§ 371 Date: Nov. 12, 1998

§ 102(e) Date: Nov. 12, 1998

[87] PCT Pub. No.: WO97/22359

PCT Pub. Date: Jun. 26, 1997

[30] Foreign Application Priority Data

Dec. 20, 1995 [DE] Germany ............ 195 49 232

[51] Int. Cl.$^7$ .......... A61K 38/19; A61K 31/675
[52] U.S. Cl. .......... 424/85.1; 514/2; 514/8; 514/76; 514/54; 514/110; 514/114
[58] Field of Search .......... 424/85.1; 514/2, 514/8, 76, 54, 110, 114

[56] References Cited

PUBLICATIONS

Neben et al. Blood, vol. 81, No. 7, 1993, pp. 1960–1967, Apr. 1993.

*Primary Examiner*—Prema Mertz
*Assistant Examiner*—Fozia Hamud
*Attorney, Agent, or Firm*—Arent Fox Kintner; Plotkin & Kahn, PLLC

[57] ABSTRACT

The invention relates to the use of G-CSF in combination with a chemotherapeutic agent (in particular, cyclophosphamide) to produce a pharmaceutical preparation for boosting the mobilization of hematopoietic stem cells from bone marrow in the treatment of diseases requiring peripheral stem cell transplantation. The claimed combination results in more efficient leukapheresis, e.g. before myeloblative or myelotoxic therapy.

7 Claims, No Drawings

COMBINATION OF G-CSF WITH A CHEMOTHERAPEUTIC AGENT FOR STEM CELL MOBILIZATION

The present invention relates to the novel use of G-CSF and a chemotherapeutic agent or a combination of chemotherapeutic agents to produce a pharmaceutical preparation for enhanced mobilization of hematopoietic stem cells in the treatment of diseases requiring peripheral stem cell transplantation as is the case, e.g., in high-dosage chemotherapy or bone marrow ablation by irradiation. In addition, the invention is directed to a pharmaceutical packaging unit containing G-CSF, chemotherapeutic agent(s) and informational instructions regarding the application of the G-CSF and the chemotherapeutic agent or the combination of chemotherapeutic agents for enhanced mobilization of hematopoietic stem cells prior to the onset of a corresponding therapy.

The use of high-dosage chemotherapy or bone marrow ablation by irradiation requires subsequent incorporation of hematopoietic stem cells into the patient, in which case recovery of such cells is required.

In the methods of peripheral stem cell recovery (e.g., in leukopheresis), the mobilization of bone marrow stem cells has a crucial influence on the efficiency of these methods. At present, 2–3 leukophereses are required for successful peripheral stem cell transplantation, resulting in considerable stress for the patients.

The success of treatment crucially depends on the mobilization of the bone marrow stem cells, the subsequent return of which permitting to achieve reconstitution of a functioning hematopoietic system.

Numerous substances capable of effecting such a mobilization are known, e.g., G-CSF (granulocyte colony stimulating factor).

Some chemotherapeutic agents are also known to possess the ability of mobilizing bone marrow stem cells (Richman et al., Blood, Vol. 47, No. 6. 1031 (1976)).

Various documents also describe the combination of G-CSF with other active substances. Thus, combined treatments using antibiotics are known from EP-A-0,648,501 and WO-A-95/28178. The U.S. Pat. No. 5,422,105 reports the combination with one or more antimicrobial substances such as antiviral, antifungal or antibacterial agents in order to enhance the effect of a CSF-1 therapy. In addition, there have been investigations on the use of G-CSF in association with high-dosage chemotherapies in autologous bone marrow transplantations (Lymphokine Cytokine Res. (1994), 13(6), 383–90; and Leukemia and Lymphoma (1995), 19(5–6), 479–84).

In other investigations related to bone marrow transplantations, Shirota et al. have determined that cyclophosphamide which is known as cytostatic agent facilitates the permeability of the endothelial barrier for stem cells (Exp. Hematol. 19, 369–373 (1991)).

As the required number of leukophereses is extremely stressing for the patient in the run-up to the treatment of particular diseases, e.g., in preparing a myeloablative or myelotoxic therapy, the invention was based on the object of achieving a superior yield of stem cells or a decrease in the number of leukophereses via enhanced mobilization of stem cells.

Surprisingly, it has now been found that an unexpectedly high stem cell concentration in blood can be achieved when administering G-CSF in combination with a chemotherapeutic agent (chemotherapeutic agents).

Therefore, the invention is directed to the use of G-CSF and a chemotherapeutic agent or a combination of chemotherapeutic agents to produce a pharmaceutical preparation for enhanced mobilization of hematopoietic stem cells in the treatment of diseases requiring peripheral stem cell transplantation, wherein G-CSF and the chemotherapeutic agent are present formulated in separate administration forms, so that they can be taken out separately and administered successively according to the optimum application regimen. According to the invention, it is preferred to apply the G-CSF prior to the onset of the administration of chemotherapeutic agents in order to enhance the mobilization of hematopoietic stem cells.

The combined use according to the invention of G-CSF and chemotherapeutic agent relates to all those diseases requiring recovery of stem cells from the blood for subsequent peripheral transplantation, particularly tumor diseases.

According to the present invention, G-CSF prepared using recombinant methods and variants thereof may be used. The term G-CSF or G-CSF variant according to the present invention encompasses all naturally occurring variants of G-CSF, as well as G-CSF proteins derived therefrom, modified by recombinant DNA technology, particularly fused proteins containing other protein sequences in addition to the G-CSF portion. Particularly preferred in this meaning is a G-CSF mutein having an N-terminal Met residue at position 1, which is suited for expression in prokaryotic cells. Similarly suitable is a recombinant G-CSF variant free of methionine which may be prepared according to WO-A-91/11520. The term "G-CSF variant" is understood to comprise those G-CSF molecules wherein one or more amino acids may be deleted or replaced by other amino acids, with the essential properties of G-CSF, particularly the ability to mobilize bone marrow cells, being largely retained. Suitable G-CSF muteins are described in EP-A-0,456,200, for example.

As chemotherapeutic agents in the meaning of the invention those therapeutic agents may be used which open the endothelial barrier, rendering it permeable for stem cells. Hereinbelow, chemotherapeutic agents are understood to be exogenous substances suited and used to damage or destroy microorganisms, parasites or tumor cells. Here, in particular, cytostatic agents or derivatives thereof from the following group of cytostatic agents may be mentioned: alkylating agents such as, e.g., cyclophosphamide, chlorambucil, melphalan, busulfan, N-mustard compounds, mustargen; metal complex cytostatic agents such as metal complexes of platinum, palladium or ruthenium; antimetabolites such as methotrexate, 5-fluorouracil, cytorabin; natural substances such as vinblastine, vincristine, vindesine, etc.; antibiotic agents such as dactinomycin, daunorubicin, doxorubicin, bleomycin, mitomycin, etc.; hormones and hormone antagonists such as diethylstilbestrol, testolactone, tamoxifen, aminoglutethimide, and other compounds such as, e.g., hydroxyurea or procarbacin, as well as corticoids such as prednisolone, with cyclophosphamide being particularly preferred.

G-CSF may be administered using standard administration forms, with injection solutions being preferred. Water is preferably used as injection medium which includes adjuvants common in injection solutions, such as stabilizers, solubilizers and buffers. For example, such adjuvants are tartrate and citrate buffers, ethanol, complexing agents such as ethylenediaminetetraacetic acid and the non-toxic salts thereof, high molecular weight polymers such as liquid polyethylene oxide for viscosity control. Liquid vehicles for injection solutions must be sterile and are preferably filled into ampoules.

The chemotherapeutic agents may be applied in liquid or solid form on the enteral or parenteral route. Here, the standard administration forms such as tablets, capsules, coated tablets, syrups, solutions and suspensions are possible.

The dosage may depend on various factors such as mode of application, species, age, or individual condition. According to the invention, from 5 to 300 μg/kg/day of G-CSF sc. is applied. The administration of G-CSF is effected once per day over two to three days. The administration of chemotherapeutic agent(s) is initiated either immediately after the second or third G-CSF injection or on the fourth day. According to the invention, from 0.05–100 mg/kg/day of chemotherapeutic agent(s) is/are administered.

Surprisingly, it was determined that administration of G-CSF prior to opening of the endothelial barrier induced by chemotherapeutic agents significantly increases the stem cell mobilization and thus, can improve leukopheresis efficiency.

By administering G-CSF prior to administration of the chemotherapeutic agent(s), a massive granulopoiesis in the spleen and a substantial increase of the spleen weight could be observed which, according to Bungart et al., Brit. J. Haem. 76, 174–179, 1990, is attributable to the stem cell mobilization.

In addition, administration of G-CSF and a chemotherapeutic agent in the run-up to a, e.g., antitumor therapy offers the opportunity of recovering the stem cells mobilized in large amounts from the blood with higher efficiency (e.g., using leukopheresis), then performing the antitumor therapy using a cytostatic agent or irradiation and subsequently, conducting the peripheral stem cell transplantation.

The invention is also directed to a pharmaceutical packaging unit including at least three spatially separated components, the first component being a standard administration form of G-CSF, the second component representing a standard pharmaceutical administration form of a chemotherapeutic agent or a combination of chemotherapeutic agents, and the third component comprising informational instructions for the administration of G-CSF prior to administration of the chemotherapeutic agent (chemotherapeutic agents) for enhanced mobilization of hematopoietic stem cells.

Where G-CSF is administered in combination with, e.g., two chemotherapeutic agents, these chemotherapeutic agents may be formulated separately or together, so that the packaging unit consists of either three or four spatially separated components.

Without intending to be limiting, the invention will be illustrated in more detail in the following embodiment.

Embodiment

Using mice, the in vivo interactions between rh G-CSF and cyclophosphamide (CY) applications regarding the effects of various schemes of treatment on the hematopoietic capacity of femoral cells, the femoral bone marrow and spleen histologies, and the leukocyte number (WBC) were examined.

The following test groups were examined:

G-CSF/CY group: G-CSF application was effected on three successive days prior to cyclophosphamide (CY) administration; the third injection was effected immediately before CY administration.

CY/G-CSF group: corresponding to the present clinical practice, G-CSF was applied beginning 24 hours after CY injection.

CY group: treatment was effected using CY alone.

Control group.

1. Materials a) Animals

Female NMRI mice were purchased. Initially, their body weight was approximately between 26 and 28 g. The animals were fed on pellets and had ad libitum access to feed and drinking water.

They were kept separately at room temperature (23±1° C.) and a relative humidity of 55% (50–70%). The room air was exchanged approximately 10 times per hour. The day/night rhythm was held constant, with light/dark periods of 12 hours each, beginning at 6 a.m. A light intensity of about 60 lux was provided throughout the room during the light period. The health condition of the animals was recorded daily, and cleaning was effected at regular intervals. Categorizing of the animals into the individual test groups can be inferred from Table 1.

b) Reagents

Recombinant human (rh) G-CSF, cyclophosphamide

2. Methods a) Peripheral Leukocyte Number (WBC)

The measurements were conducted using an analyzer. Under anesthesia, 25 μl of native whole blood was withdrawn from the postorbital plexus using heparinized glass capillaries, diluted with 3.75 ml of an isosmotic solution, and analyzed with respect to WBC.

b) Femoral Bone Marrow Cell Number (BMC)

After 4 weeks of treatment or after a two weeks period free of treatment, respectively, the femora of 5 animals (n=8, G-CSF/CY group) from the various test groups were collected. They were opened aseptically at the proximal and distal ends. Rinsing the bone marrow cavities with 1.5 ml of MEM (supplemented with penicillin/streptomycin and L-glutamine), the bone marrow cells were recovered using syringes equipped with adapters. Except for the G-CSF/CY test group wherein both femora of from 3 to 8 animals were analyzed, one femur of each animal was examined. The cells were counted in an autolyzer system.

c) CFU-C Test (Colony-Forming Units Culture)

The femoral bone marrow cell number was adjusted to $2.5 \times 10^{-6}$ cells/ml in MEM (flow). 0.2 ml of this suspension was mixed with 0.5 ml of horse serum, 0.1 ml of thioglycerol (20 mM, diluted 1:4 with MEM), 1.0 ml of methylcellulose (2% in MEM), 0.6 ml of MEM (flow), and 0.1 ml of either additional medium or standardized stimulated mouse serum (1:200 dilution of serum, withdrawn 3 hours after ip. administration of 2.5 mg/kg lipopolysaccharide (LPS)) or 5 ng/ml rhG-CSF. The well-mixed semi-solid suspension was pipetted into Petri dishes 4 cm in diameter and incubated for 6 days at 37° C., 5% $CO_2$ and 95% r.h.. After addition of 0.5 ml of p-iodonitrotetrazolium violet solution (0.5 mg/ml PBS), the dishes were incubated for another 24 hours. The colonies were counted using a colony counter and standardized to $10^6$ bone marrow cells.

d) Tissue Preparation and Histological Test

The animals were sacrificed on the day of final administration of the compounds, and spleen tissue as well as one femoral bone of each animal were fixed in 10% neutral-buffered formaldehyde solution. The bone samples were decalcified over two weeks in 5% formic acid, dissolved in formaldehyde/distilled water. Spleen and bones were stored routinely in paraffine, cut to 4 μm thickness, and stained with hematoxylin-eosin (HE), as well as with PAS. Bone marrow and spleen were semi-quantitatively evaluated with respect to cell quality, myelofibrosis and cellular necrosis using a light microscope.

e) Statistics

The various test groups were compared with control animals with respect to the end points of BMC, CFU-C response to G-CSF, CFU-C response to serum, and spleen weight. Repeated measurements of WBC (basis: 1, 2, 3, and 4 weeks) were transformed into an end point, based on the individual AUC approximation according to Zerbe et al., Biometrics 33, 653, 1992. Investigations for approximate normal distribution of WBC and spleen weight were analyzed according to the Welch T Test (Welch, Biometrika 34, 28, 1947) because a notable variance in the heterogeneity was observed. Due to the absence of an approximately normal distribution for the other end points, a permutational U test according to Mehta et al., CYTEL Software Corp. Turbo Version, Cambridge, U.S.A., 1992, was conducted. The method of multiple end point analysis was carried out for the end points of CFU-C, when administering G-CSF or serum, and the spleen weight. The end points after the period with no treatment (week 6) were analyzed for reversibility using a method according to Dunnett, JASA 50, 1096, 1955, which may be used for comparing with the controls. The calculations were performed using SAS, Version 6.10 (SAS/STAT: Changes and enhancements, Release 6.10, SAS Institute, 1994) and Statxact (Mehta et al., see above).

3. Results a) Effects Regarding the Femoral Bone Marrow Cell Number (BMC)

The effects of various treatment regimens are included in Table 2. CY alone reduced the bone marrow cell number to about 60% of the control. Both combinations of CY and G-CSF reduced the number to about 30% of the control. Two weeks after the treatment was completed, however, the animals from the CY/G-CSF test group again showed increasing bone marrow cell numbers compared to the number immediately after treatment. At the end, they reached about 50% of the control. The other three test groups did not show any relevant changes during the follow-up period with no treatment.

b) Effects in the CFU-C Test

The response to serum of LPS-treated mice and to G-CSF was massively decreased in the CY group, compared to the bone marrow cells of the controls. A marked decrease was observed in G-CSF/CY treatment, while the CY/G-CSF test group showed increased colony formation in the presence of serum of LPS-treated mice and in the presence of G-CSF.

After a 2 weeks period with no treatment, the differences between both G-CSF groups and the controls became smaller. The proliferative response to serum of LPS-treated mice in the CY group showed after this period an extraordinary elevation compared to the marked decrease at the end of the treatment period.

c) Bone Marrow Histology

At the end of the treatment period: The granulopoietic cell density in the hematopoietically active areas of the femoral bone marrow markedly increased in both groups that had been treated with G-CSF and CY compared to the control animals and the CY test group (Table 3). The effect is particularly apparent in the G-CSF/CY test group. However, it can be seen that a clearly perceptible decrease of the hematopoietic areas as a result of fibrosis and ossification occurred in the various treatment groups. The CY group did not show any signs of increased granulopoiesis.

The stimulation of granulopoiesis due to administration of G-CSF prior to CY gave rise to all stages of maturity, whereas maturity stages were observed with less abundance upon administration of CY/G-CSF. The occurrence of single cell necroses was moderate in the G-CSF/CY and CY test groups and low in the CY/G-CSF group.

d) Effects on the Spleen

Histology at the end of treatment: Light microscopy of spleen tissue revealed a marked increase of granulopoietic cells after 4 weeks of treatment in both groups which had received G-CSF in combination with CY (Table 4). Granulopoiesis comprised all stages of granulopoietic cell maturation most markedly in the G-CSF/CY group. The granulopoietic cell proliferation in the CY/G-CSF group mainly consisted of myeloblastic cells, maturity stages were barely observable. The considerable increase of granulopoietic cells occurred in association with a considerable rearrangement of the spleen organic structure. Single cell necroses were observed in the G-CSF/CY group and to a lesser extent, in the animals of the CY/G-CSF test group. The spleen of animals that had been treated with CY alone showed a slight cellular decline in the follicles and the reticulum. During a 2 weeks period with no treatment, the changes returned to normal. In those groups, however, where G-CSF and CY had been administered, there were signs of a slightly increased hematopoietic stimulation in the form of elevated granulopoiesis, erythropoiesis and megakaryopoiesis.

e) Effects on Spleen Weight

An enormous increase (more than 3.3 fold of the control) was determined at the end of the treatment period in those animals that had been treated with G-CSF/CY (Table 5), and an 1.8 fold increase compared to the control was observed in the CY/G-CSF test group. There were no relevant effects on the spleen weight in the CY group.

f) WBC

Blood samples were taken prior to the first treatment and then once per week immediately before administering CY (or placebo). Thus, the blood samples in the G-CSF/CY test group were taken after the administration of G-CSF. Additional blood samples were collected at the end of the treatment period (after 4 weeks) and after the two weeks period with no treatment, respectively.

As is apparent from Table 6, there were no relevant differences in the WBC between the controls and the CY and CY/G-CSF groups.

During week 1, the G-CSF/CY test group showed a WBC slightly elevated above the upper limit of normal; during the following weeks 2, 3 and 4, there was a substantial WBC increase (from 7- to 8 fold of the control); complete reversal of this effect could be observed after the two weeks period with no treatment.

On the whole, it can be seen that the extent of osteomyelofibrosis and multifocal ossification after the treatment using G-CSF/CY was definitely higher compared to other methods. Furthermore, massive granulopoiesis and a substantial increase in spleen weight could be observed in this test group, emphasizing the increased stem cell mobilization.

The reduced CFU-C capacity of bone marrow cells after G-CSF/CY administration must be regarded as a result of an increased mobilization of progenitor cells into the blood. This is supported by the multiple end point analysis.

TABLE 1

Dosage and assignment of animals to test group

| Test groups | Weekly dosage during weeks 1 to 4 | Number of animals per test group |
|---|---|---|
| G-CSF/CY group | | |
| G-CSF administration sc. followed by | 250 μg/kg on 3 successive days + | (n = 8) |

TABLE 1-continued

Dosage and assignment of animals to test group

| Test groups | Weekly dosage during weeks 1 to 4 | Number of animals per test group |
|---|---|---|
| CY administration ip. (n = 16) | 50 mg/kg immediately after G-CSF administration on the 3rd day | |
| CY/G-CSF group | | |
| CY administration ip. after 24 hrs followed by G-CSF administration (n = 10) | 50 mg/kg + 250 μg/kg on 3 successive days | (n = 5) |
| CY group | | |
| ip. (n = 10) | 50 mg/kg | (n = 5) |
| Control group | | |
| (n = 10) | 0.9% NaCl solution ip. and sc. | (n = 5) |

After 6 weeks (2 weeks with no treatment) another examination was conducted in satellite groups.

TABLE 2

Bone marrow cell numbers (BMC) of mice after 4 weeks of treatment and after a 2 weeks period with no treatment
(† = animal died untimely)

| Treatment group | BMC (× 10⁶/femur) 4 weeks treatment | BMC (× 10⁶/femur) After 2 weeks without treatment |
|---|---|---|
| Control | 13.2 | 14.7 |
| | † | 15.9 |
| | 8.6 | 20.6 |
| | 21.3 | 18.1 |
| | 18 | 16.6 |
| Median value | 15.28 | 17.18 |
| CY alone | 13.6 | 12.7 |
| | 7.8 | 8.3 |
| | 13 | 6.1 |
| | 7.6 | 10.3 |
| | 2.9 | 9.9 |
| Median value | 8.98 | 9.46 |
| G-CSF + CY | 5.6 | 4.7 |
| | 7.4 | 9.5 |
| | 0.75 | 3.4 |
| | 2.1 | 0.48 |
| | 1.6 | 1.32 |
| | 7.8 | 2.2 |
| | 0.65 | 0.55 |
| | 1.2 | 0.72 |
| Median value | 3.39 | 2.86 |
| CY + G-CSF | 3.5 | 9.4 |
| | 3.5 | 7.4 |
| | 7.3 | 3.5 |
| | 7.9 | 9.1 |
| | 0.25 | 12.5 |
| Median value | 4.49 | 8.38 |

TABLE 3

Histopathological findings in bone marrow (femur)

| | CY | G-CSF/CY | CY/G-CSF |
|---|---|---|---|
| After 4 weeks treatment | | | |
| Cellular decline | ++ | (+) | +/++ |
| Fat cells | +/++ | (+) | + |
| Hyperemia | — | — | + |
| Increased single cell necrosis | ++ | ++ | + |
| Stimulated granulopoiesis | ±0 | +++ | ++ |
| Osteomyelofibrosis or multifocal ossification | 1.5, +++ | 8/8, ++/+++ | |
| After 2 weeks with no treatment | | | |
| Fat cells | (+) | (+) | (+) |
| Stimulated granulopoiesis | (+) | +/++ | +/++ |
| Osteomyelofibrosis or multifocal ossification | 3/5, (+)/+ | 8/8, +++ | 3.5, +/++ |

(+) = minimal
+ = faint
++ = moderate
+++ = marked

TABLE 4

Histopathological findings in the spleen

| | CY alone | G-CSF/CY | CY/G-CSF |
|---|---|---|---|
| State after 4 weeks treatment | | | |
| Cellular decline Follicle cells (lymphocytes) | + | — | — |
| Cellular decline Reticulum cells | + | — | — |
| Stimulated granulopoiesis | — | +++[1] | +/++[2] |
| Loss of follicle structure | | +++ | +/++ |
| Increased single cell necrosis | | ++ | (+) |
| After 2 weeks with no treatment | | | |
| Stimulated hematopoiesis | — | + | + |

[1] All maturity stages
[2] Mainly myeloblastic cells

TABLE 5

Spleen weight
(† = animal died untimely)

| Treatment group | Spleen weight (g) after 4 weeks treatment | Spleen weight (g) after 2 weeks with no treatment |
|---|---|---|
| Control | 0.141 | 0.135 |
| | † | 0.090 |
| | 0.148 | 0.127 |
| | 0.410 | 0.133 |
| | 0.161 | 0.150 |
| Median value | 0.215 | 0.127 |
| CY alone | 0.107 | 0.183 |
| | 0.100 | 0.121 |
| | 0.174 | 0.235 |
| | 0.082 | 0.199 |
| | 0.189 | 0.133 |
| Median value | 0.130 | 0.174 |
| G-CSF + CY | 0.523 | 0.194 |
| | 0.448 | 0.248 |
| | 0.497 | 0.181 |
| | 0.477 | 0.262 |
| | 0.523 | 0.219 |

TABLE 5-continued

Spleen weight
(† = animal died untimely)

| Treatment group | Spleen weight (g) after 4 weeks treatment | Spleen weight (g) after 2 weeks with no treatment |
|---|---|---|
| | 0.492 | 0.261 |
| | 0.483 | 0.153 |
| | 0.486 | 0.273 |
| Median value | 0.491 | 0.224 |
| CY + G-CSF | 0.263 | 0.177 |
| | 0.218 | 0.228 |
| | 0.225 | 0.208 |
| | 0.324 | 0.218 |
| | 0.254 | 0.232 |
| Median value | 0.257 | 0.213 |

TABLE 6

Leukocyte number (WBC)
(† = animal died untimely)

| | | WBC ($\times 10^6/\mu l$) Time (weeks) | | | | | |
|---|---|---|---|---|---|---|---|
| Treatment group | Animal number | 0 | 1 | 2 | 3 | 4 | 6 |
| Control | 1 | 5.6 | 5.2 | 9.4 | 3.3 | 6.6 | — |
| | 2 | 10 | 6.3 | 6.9 | † | † | † |
| | 3 | 7 | 4.8 | 7 | 3.4 | 6.8 | — |
| | 4 | 7.6 | 7.6 | 7.7 | 3.9 | 7.7 | |
| | 5 | 9.1 | 6 | 11 | 3.5 | 6.3 | |
| | 6 | 8.4 | 5.1 | 9.5 | 6.2 | 7.5 | 4.5 |
| | 7 | 2.5 | 2.3 | 5.3 | 5 | 5.7 | 3 |
| | 8 | 9.5 | 7.3 | 12.2 | 8.5 | 13.7 | 7.8 |
| | 9 | 6.3 | 4.3 | 8.8 | 4.2 | 10.1 | 4.5 |
| | 10 | 6 | 5.9 | 8.5 | 5.9 | 8 | 6.4 |
| Median value | | 7.20 | 5.48 | 8.63 | 4.88 | 8.04 | 5.24 |
| CY alone | 1 | 4.8 | 2.9 | 5 | 7.6 | 4 | — |
| | 2 | 9 | 7.1 | 5.3 | 2.7 | 2.8 | — |
| | 3 | 8.6 | 5.9 | 7.3 | 5.2 | 7 | — |
| | 4 | 6.3 | 4.8 | 6.3 | 6.1 | 4.8 | — |
| | 5 | 5.3 | 4.5 | 4.9 | 8.6 | 2.9 | — |
| | 6 | 6.4 | 5 | 5.1 | 6.7 | 4.1 | 3.6 |
| | 7 | 6.8 | 4.7 | 4.9 | 5 | 3.6 | 3.2 |
| | 8 | 5.6 | 5.7 | 4.8 | 4.1 | 3.7 | 4.6 |
| | 9 | 5.8 | 4.7 | 5.9 | 4.1 | 7.1 | 5.9 |
| | 10 | 9.4 | 6 | 7.1 | 4 | 2.8 | 5.9 |
| Median value | | 6.80 | 5.13 | 5.66 | 5.41 | 4.28 | 4.64 |
| G-CSF + CY | 1 | 6.1 | 11.7 | 27.7 | 33.4 | 39.4 | — |
| | 2 | 6.8 | 12.4 | 46.5 | 43.7 | 30.5 | — |
| | 3 | 5.6 | 11.2 | 30.3 | 58.78 | 40.6 | — |
| | 4 | 4.3 | 11.7 | 35.3 | 51.4 | 40.7 | — |
| | 5 | 6.2 | 22.4 | 62.2 | 55.4 | 66.7 | — |
| | 6 | 6.2 | 12.6 | 49.2 | 84.2 | 85.4 | — |
| | 7 | 7.1 | 16.8 | 84.8 | 105.4 | 102.3 | — |
| | 8 | 8 | 18.6 | 82 | 117.6 | 70.1 | — |
| | 9 | 3 | 5.4 | 42.7 | 15.8 | 33.3 | 2.2 |
| | 10 | 4.6 | 18.2 | 62.8 | 69 | 33.2 | 3.9 |
| | 11 | 5.8 | 10.9 | 29.1 | 40 | 33.5 | 2.7 |
| | 12 | 5 | 12.7 | 43.8 | 51.9 | 28.1 | 6.4 |
| | 13 | 5.8 | 14.6 | 28.8 | 33.4 | 20 | 4.6 |
| | 14 | 6.2 | 10.2 | 50 | 36.8 | 45.4 | 3.6 |

TABLE 6-continued

Leukocyte number (WBC)
(† = animal died untimely)

| | | WBC ($\times 10^6/\mu l$) Time (weeks) | | | | | |
|---|---|---|---|---|---|---|---|
| Treatment group | Animal number | 0 | 1 | 2 | 3 | 4 | 6 |
| | 15 | 8.6 | 20.2 | 30 | 36.2 | 25.3 | 5.2 |
| | 16 | 5.9 | 12.8 | 26.8 | 45.5 | 54.8 | 4.9 |
| Median value | | 6.00 | 14.04 | 48.08 | 55.16 | 44.60 | 4.19 |
| CY + G-CSF | 1 | 6.7 | 6.1 | 6.9 | 9.5 | 12.68 | — |
| | 2 | 9.1 | 7.1 | 11.08 | 11.6 | 3.78 | — |
| | 3 | 9.1 | 11.1 | 4.5 | 9.6 | 5.9 | — |
| | 4 | 6.9 | 5.2 | 10.4 | 16.6 | 5 | — |
| | 5 | 6.3 | 3.9 | 7 | # | 11.6 | — |
| | 6 | 9.6 | 8.3 | 5 | 6.9 | 4.1 | 4.6 |
| | 7 | 6.6 | 6.3 | 8.6 | 7.1 | 7.5 | 4.2 |
| | 8 | 6.1 | 4.4 | 5.4 | 3.8 | 3.18 | 2.4 |
| | 9 | 10.3 | 7.6 | 4.8 | 4.2 | 6.2 | 3.7 |
| | 10 | 8.2 | 6.5 | 5.4 | 6.2 | 4.3 | 3.2 |
| Median value | | 7.89 | 6.65 | 6.91 | 8.39 | 6.42 | 3.62 |

What is claimed is:

1. A method of treating a disease requiring peripheral stem cell transplantation in a patient in need of such treatment, comprising administering to the patient a hematopoietic stem cell mobilizing-effective amount of G-CSF; and thereafter administering to the patient a disease treating-effective amount of at least one chemotherapeutic agent.

2. The method of claim 1, wherein the disease is a tumor disease.

3. The method of claim 1, wherein the G-CSF is recombinant G-CSF.

4. The method of claim 1, wherein the at least one chemotherapeutic agent opens the endothelial barrier of the patient to render the endothelial barrier permeable for stem cells.

5. The method of claim 1, wherein the at least one chemotherapeutic agent is cyclophosphamide.

6. The method of claim 1, wherein the G-CSF is administered once per day over 2–3 consecutive days, and the chemotherapeutic agent is administered immediately after the final administration of G-CSF, or on a fourth consecutive day.

7. A pharmaceutical kit, comprising a first component comprising G-CSF;

a second component comprising at least one chemotherapeutic agent; and a third component comprising instructions for the administration of the G-CSF prior to the onset of administration of the at least one chemotherapeutic agent.

* * * * *